United States Patent
Li et al.

(10) Patent No.: US 10,004,261 B2
(45) Date of Patent: Jun. 26, 2018

(54) ATOMIZING DEVICE, BATTERY ASSEMBLY, AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Xianming Wang, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 664 days.

(21) Appl. No.: 14/501,022

(22) Filed: Sep. 29, 2014

(65) Prior Publication Data

US 2015/0101626 A1    Apr. 16, 2015

(30) Foreign Application Priority Data

Oct. 15, 2013    (CN) .............................. 201310480893

(51) Int. Cl.
| | | |
|---|---|---|
| A24F 47/00 | (2006.01) | |
| A61M 11/04 | (2006.01) | |
| A61M 15/06 | (2006.01) | |
| H01M 2/10 | (2006.01) | |
| A61M 16/10 | (2006.01) | |

(52) U.S. Cl.
CPC ......... *A24F 47/008* (2013.01); *A61M 11/042* (2014.02); *A61M 15/06* (2013.01); *H01M 2/105* (2013.01); *A61M 16/1045* (2013.01)

(58) Field of Classification Search
None
See application file for complete search history.

(56) References Cited

U.S. PATENT DOCUMENTS

| | | | |
|---|---|---|---|
| 2014/0332019 A1* | 11/2014 | Liu | ........................ A61M 15/06 131/329 |
| 2014/0366898 A1* | 12/2014 | Monsees | ............... A24F 47/008 131/329 |
| 2015/0013701 A1* | 1/2015 | Liu | ........................ A24F 47/008 131/329 |
| 2015/0053218 A1* | 2/2015 | Liu | ........................ A61M 11/042 131/329 |

* cited by examiner

*Primary Examiner* — Joseph S Del Sole
*Assistant Examiner* — Manley L Cummins, IV
(74) *Attorney, Agent, or Firm* — Cheng-Ju Chiang

(57) ABSTRACT

An exemplary atomizing device includes an atomizing sleeve, a liquid chamber in the atomizing sleeve, an atomizing assembly, a first connector arranged at one end of the atomizing sleeve. The liquid chamber is configured for reserving tobacco liquid. The atomizing assembly includes a liquid conducting component and a heating wire wound around the liquid conducting component. The liquid conducting component is configured for absorbing the tobacco liquid from the liquid chamber. The first connector is integrally formed, and includes an insulated body, an inner electrode and an outer electrode fixed in the insulated body. The insulated body, the inner electrode and the outer electrode are coaxially arranged. Two ends of the heating wire are connected to the inner electrode and the outer electrode respectively. In addition, the present disclosure also relates to a battery assembly, and an electronic cigarette using the atomizing device and the battery assembly.

14 Claims, 8 Drawing Sheets

US 10,004,261 B2

ATOMIZING DEVICE, BATTERY ASSEMBLY, AND ELECTRONIC CIGARETTE HAVING SAME

TECHNICAL FIELD

The present invention relates to electronic cigarettes, and particularly to an atomizing device, a battery assembly, and an electronic cigarette using same.

BACKGROUND ART

A typical electronic cigarette includes an atomizing device and a battery assembly threadedly coupled to the atomizing device. The atomizing device includes a screw sleeve at one end, a tubular electrode arranged in the screw sleeve, and an insulator sandwiched between the screw sleeve and the tubular electrode. When the atomizing device is engaged with the battery assembly, the screw sleeve and the tubular electrode, which respectively serve as negative and positive electrodes, are connected to the battery assembly.

However, the connecting structure between the atomizing device and the battery assembly includes a plurality of elements, and is complicated. Accordingly, it is difficult to assemble the electronic cigarette. Therefore, the production efficiency of the electronic cigarette is low and the production cost is high.

What is needed, therefore, is an atomizing device, a battery assembly, and an electronic cigarette using same, which can overcome the above shortcomings.

SUMMARY

An exemplary atomizing device includes an atomizing sleeve, a liquid chamber in the atomizing sleeve, an atomizing assembly, a first connector arranged at one end of the atomizing sleeve. The liquid chamber is configured for reserving tobacco liquid. The atomizing assembly includes a liquid conducting component and a heating wire wound around the liquid conducting component. The liquid conducting component is configured for absorbing the tobacco liquid from the liquid chamber. The first connector is integrally formed, and includes an insulated body, an inner electrode and an outer electrode fixed in the insulated body. The insulated body, the inner electrode and the outer electrode are coaxially arranged. Two ends of the heating wire are connected to the inner electrode and the outer electrode respectively.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Embodiments of the present disclosure will now be described in detail below and with references to the drawings.

Figure 1:
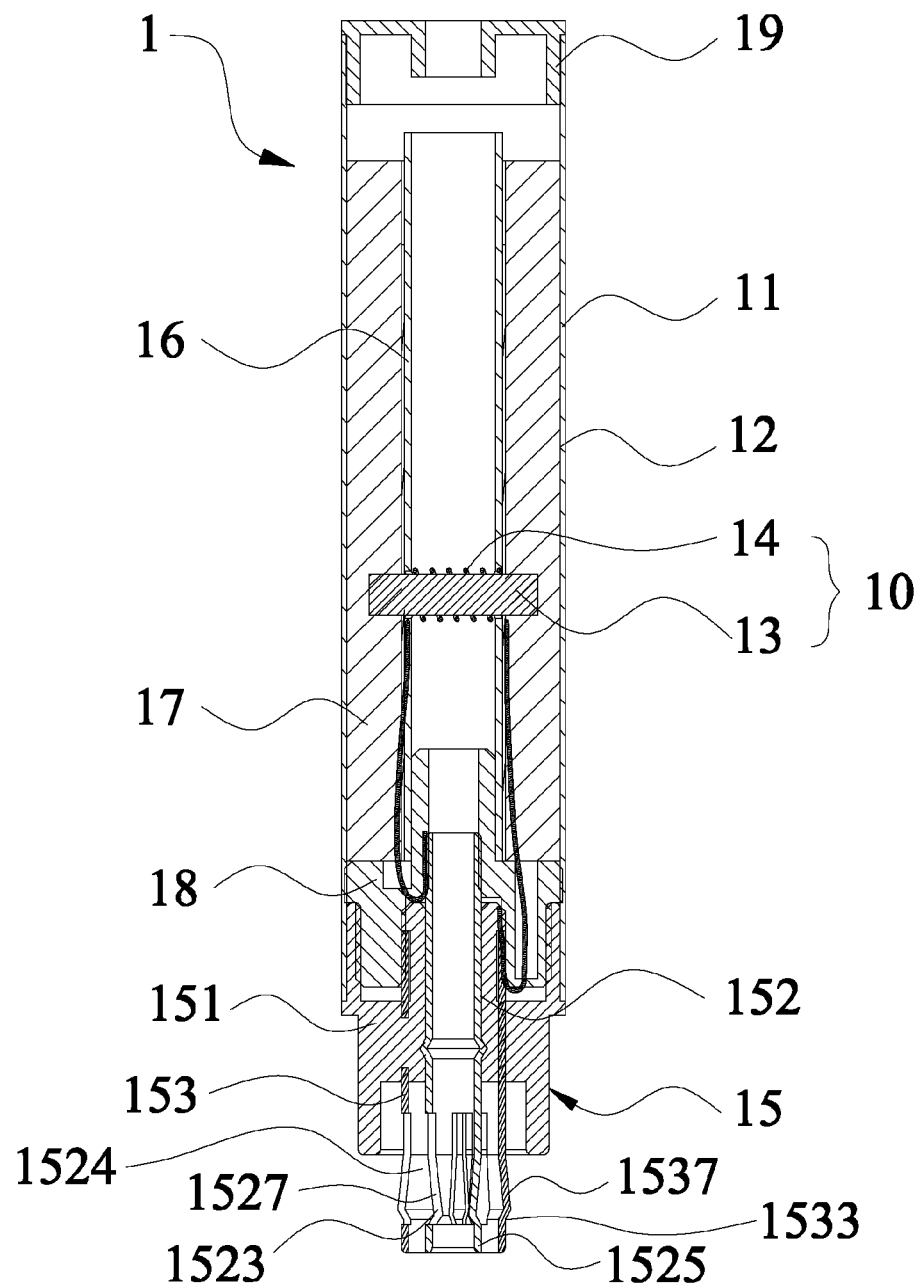
FIG. 1 is a cross-sectional view of an atomizing device according to a first embodiment.
Figure 2:
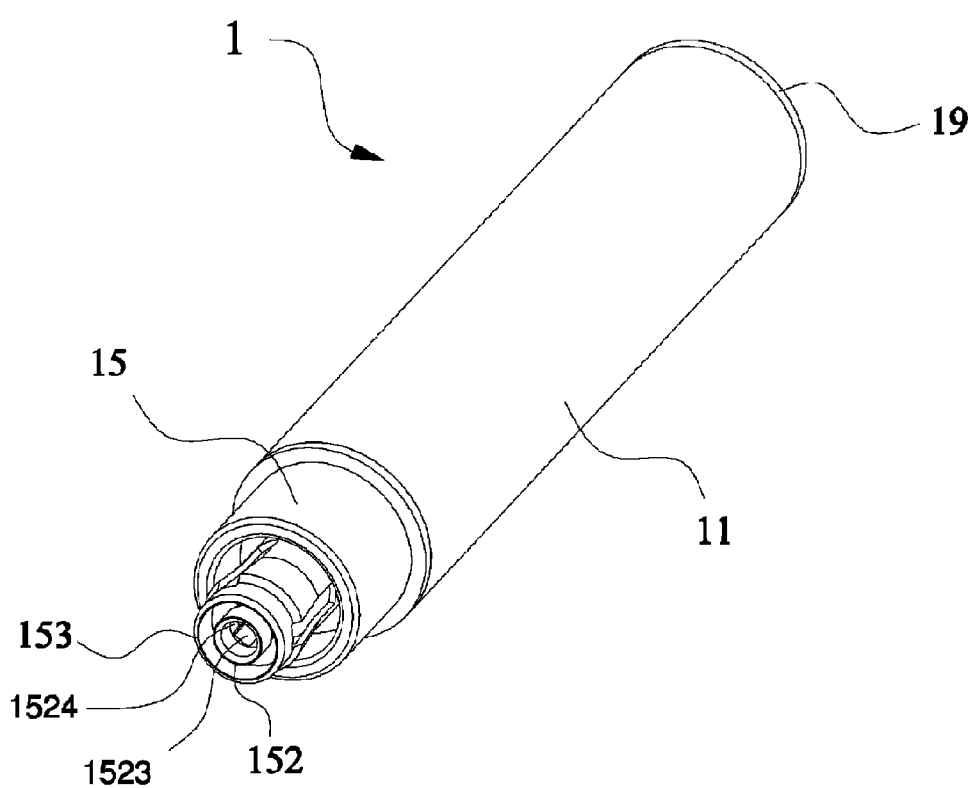
FIG. 2 is a perspective view of the atomizing device of FIG. 1.

Referring to FIGS. 1-2, an atomizing device 1 for an electronic cigarette is shown. The atomizing device 1 is configured (i.e., structured and arranged) for atomizing tobacco liquid to form aerosol. The atomizing device 1 includes an atomizing sleeve 11, a liquid chamber 12 in the atomizing sleeve 11, and an atomizing assembly 10. The atomizing assembly 10 includes a liquid conducting component 13 and a heating wire 14 wound around the liquid conducting component 13. The liquid conducting component 13 is adapted for absorbing the tobacco liquid in the liquid chamber 12, so that the heating wire 14 heats the tobacco liquid. The atomizing device 1 further includes a first connector 15 at one end. The first connector 15 is integrally formed, and includes an insulated body 151, an inner electrode 152, and an outer electrode 153. The insulated body 151, the inner electrode 152, and the outer electrode 153 are coaxially arranged. The inner electrode 152 and the outer electrode 153 are connected with two opposite ends of the heating wire 14, respectively.

Figure 3:
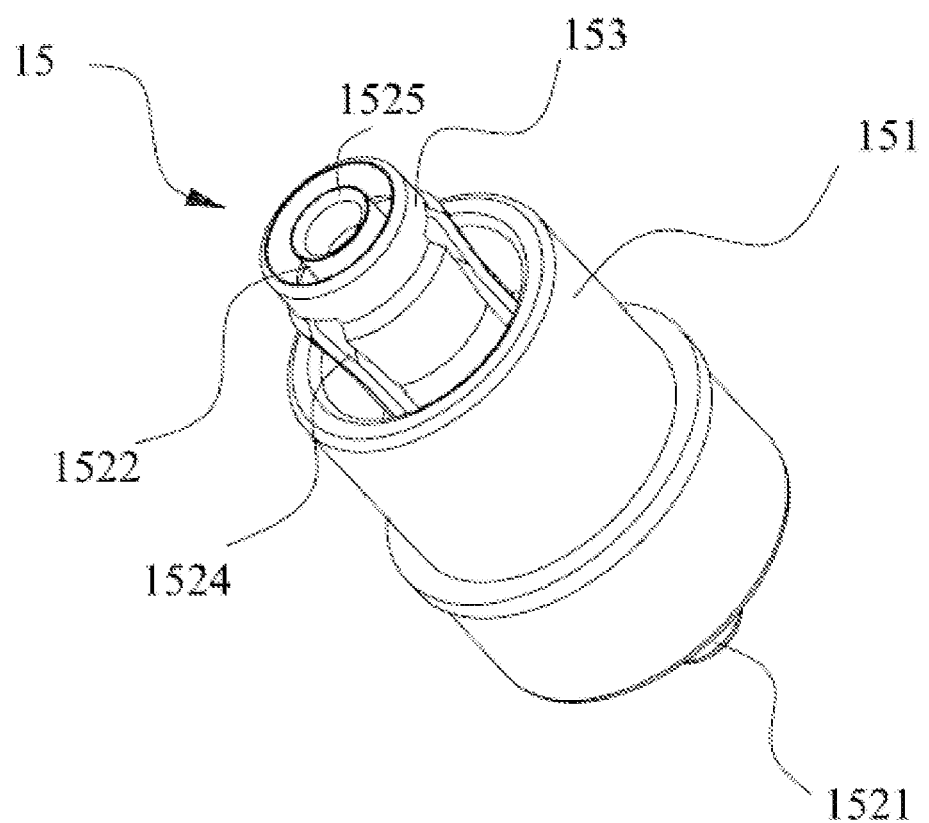
FIG. 3 is a perspective view of a first connector of the atomizing device of FIG. 1.

Also referring to FIG. 3, the inner electrode 152 includes a first end 1521 and a second end 1522. The first end 1521 is connected with one end of the heating wire 14. The second end 1522 includes a clamping portion 1527. The clamping portion 1527 includes a plurality of clamping hands 1523 for clamping and fastening a to-be-clamped object (e.g., a positive electrode).

A gap 1524 is defined between every two adjacent clamping hands 1523, so that after the first connector 15 is engaged with the to-be-clamped object, air can go into the atomizing sleeve 11 via the gap 1524. Accordingly, no additional air passage is needed, thus simplifying the structure of the atomizing device 1.

In the present embodiment, the inner electrode 152 is cylindrical. An inner diameter of the clamping portion 1527 decreases from two ends of the clamping portion 1527 to the middle of the clamping portion 1527. Thus, the clamping hands 1523 clamps the to-be-clamped object when the to-be-clamped object is inserted into the inner electrode 152. The inner electrode 152 further includes a cylindrical guiding portion 1525 at a distal end of the clamping portion 1527. An inner diameter of the guiding portion 1525 may be equal to or larger than that of the second end 1522.

The outer electrode 153 is substantially cylindrical. An engaging portion 1537 including a plurality of engaging hands 1533 is formed for engaging use. The gap 1524 is also defined between every two adjacent engaging hands 1533 corresponding to the gap 1524 defined between every two adjacent clamping hands 1523. An outer diameter of the engaging portion 1537 increases from two ends of the engaging portion 1537 to the middle of the engaging portion 1537. The insulated body 151 is made of plastic. The inner electrode 152 and the outer electrode 153 are wrapped around by the insulated body 151 to form an integral part.

In addition, the atomizing device 1 further includes an air pipe 16 coaxially arranged in the atomizing sleeve 11. The air pipe 16 may be made of glass fiber. A liquid-absorbing cotton 17 is arranged between the atomizing sleeve 11 and the air pipe 16, and is configured for absorbing the tobacco liquid. The atomizing assembly 10 is supported by the air pipe 16 in such a manner that the heating wire 14 is positioned in the air pipe 16. In this way, after the tobacco solution is absorbed by the liquid conducting component 13, and heated by the heating wire 14 to form aerosol, the aerosol flows out via the air pipe 16, and reaches a mouth of a user.

The atomizing device 1 further includes a fixing sleeve 18 arranged at one end of the atomizing sleeve 11. The fixing sleeve 18 abuts against the liquid-absorbing cotton 17. The fixing sleeve 18 is configured to engage with the first connector 15. Two ends of the heating wire 14 pass through the fixing sleeve 18, and bend to connect the inner electrode 152 and the outer electrode 153, respectively.

The atomizing device 1 further includes a mouthpiece 19 arranged at an end of the atomizing sleeve 11 away from the first connector 15. The aerosol passes through the mouthpiece 19 to reach the mouth of the user.

Figure 4:
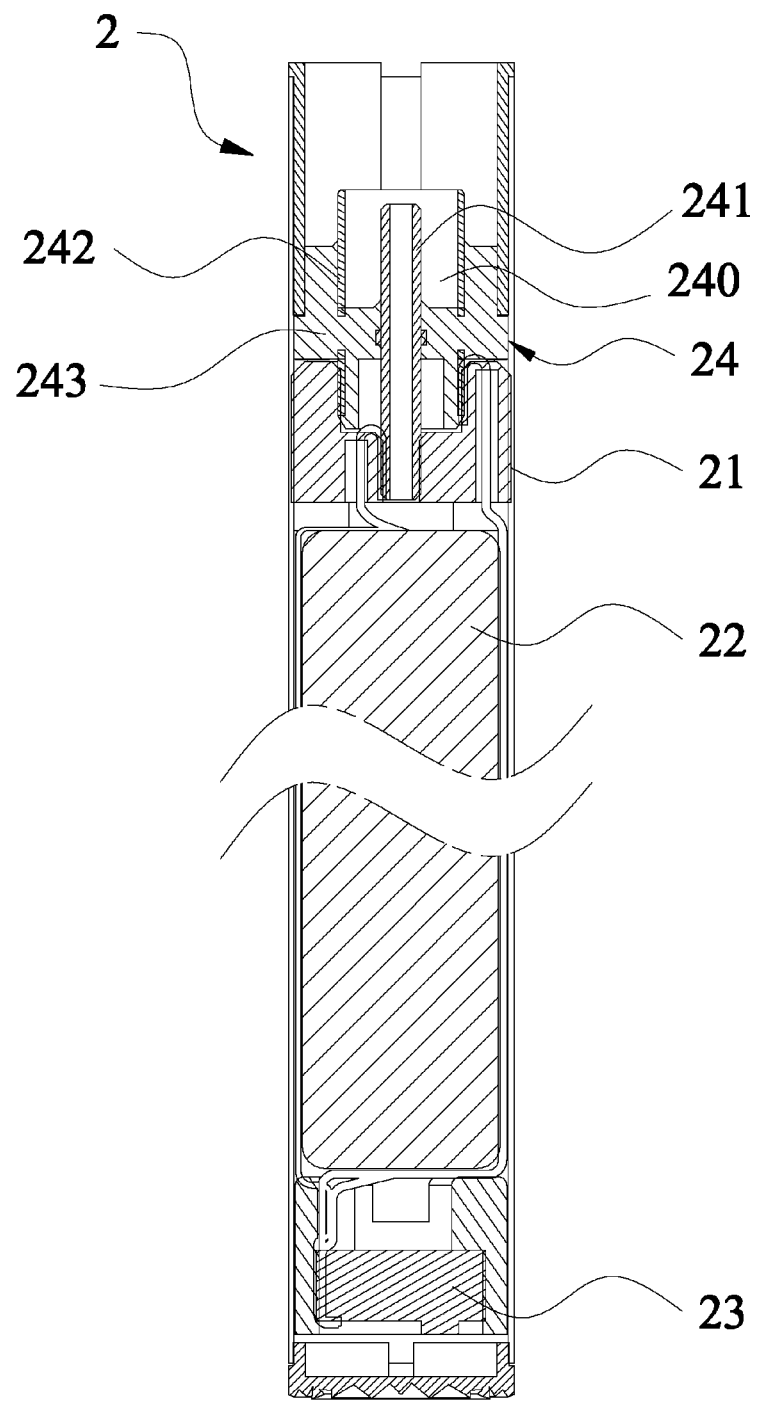
FIG. 4 is a cross-sectional view of a battery assembly according to a second embodiment.
Figure 5:
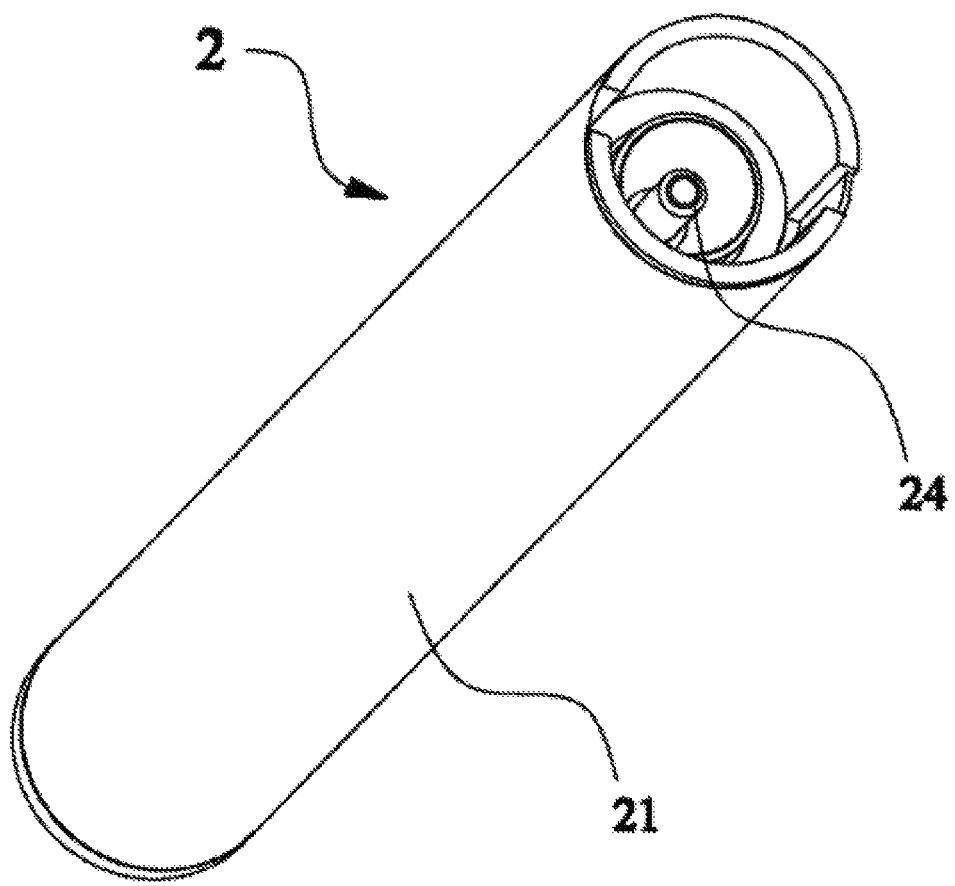
FIG. 5 is a perspective view of the battery assembly of FIG. 4.
Figure 6:
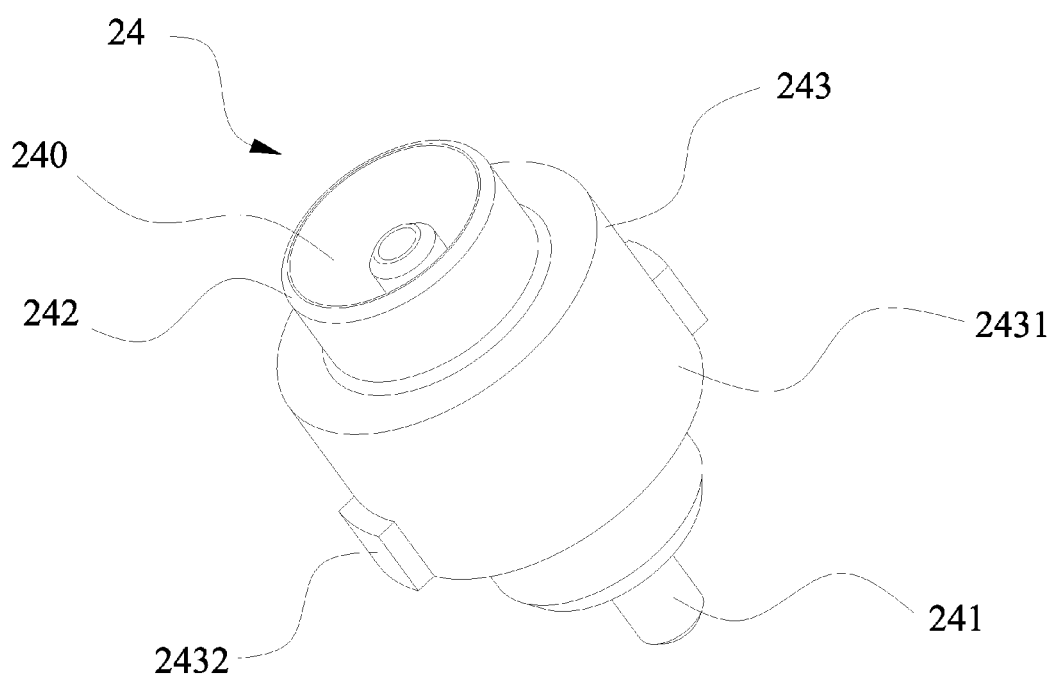
FIG. 6 is a perspective view of a second connector of the battery assembly of FIG. 4.

Referring to FIGS. 4-6, a battery assembly 2 for an electronic cigarette is shown. The battery assembly 2 includes a housing 21, a battery 22 received in the housing 21, a controller 23, and a second connector 24. The second connector 24 is integrally formed, and includes a positive electrode 241, a negative electrode 242, and an insulated medium 243. The positive electrode 241 and the negative electrode 242 are coaxially arranged. The insulated medium 243 is configured for fixing the positive electrode 241 and the negative electrode 242, and keeping them insulated from each other. The positive electrode 241 and the negative electrode 242 are connected to corresponding electrodes of the battery 22, respectively.

The positive electrode 241 and the negative electrode 242 are both cylindrical, and an annular gap 240 is defined between the positive electrode 241 and the negative electrode 242. The annular gap 240 is configured for receiving a tubular object.

The insulated medium 243 includes a side surface 2431, and at least one protrusion 2432 on the side surface 2431. The at least one protrusion 2432 is configured for securing the second connector 24 in the housing 21. In the present embodiment, the side surface 1431 is cylindrical, and the insulated medium 243 includes two opposite protrusions 2432 formed on the side surface 2431.

Figure 7:
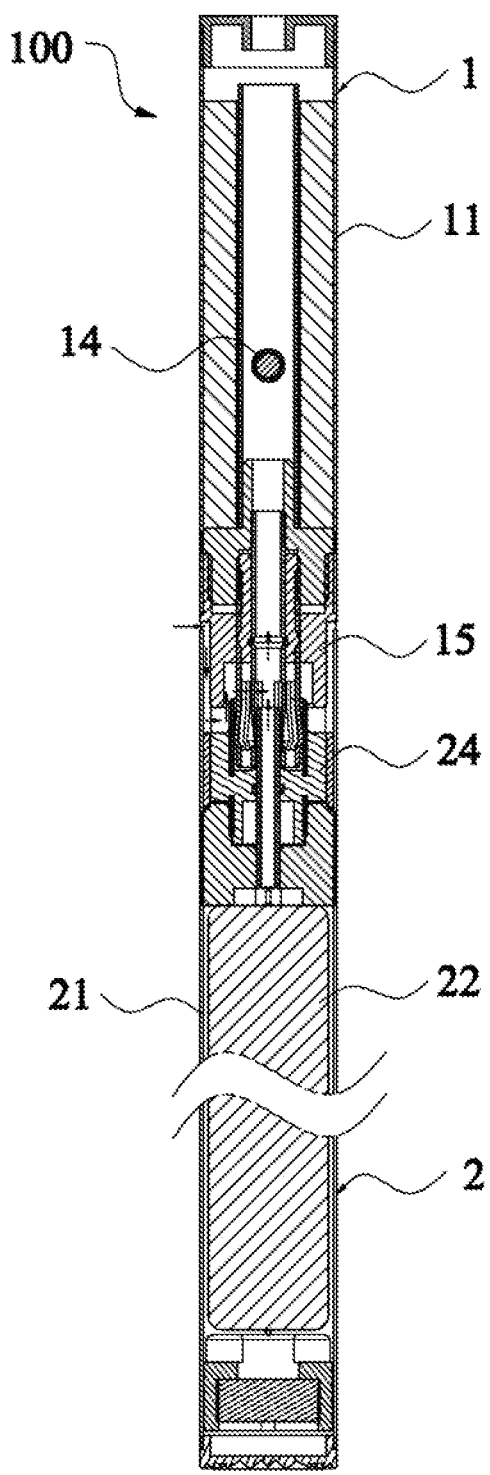
FIG. 7 is a cross-sectional view of an electronic cigarette, employing the atomizing device of FIG. 1 and the battery assembly of FIG. 4.
Figure 8:
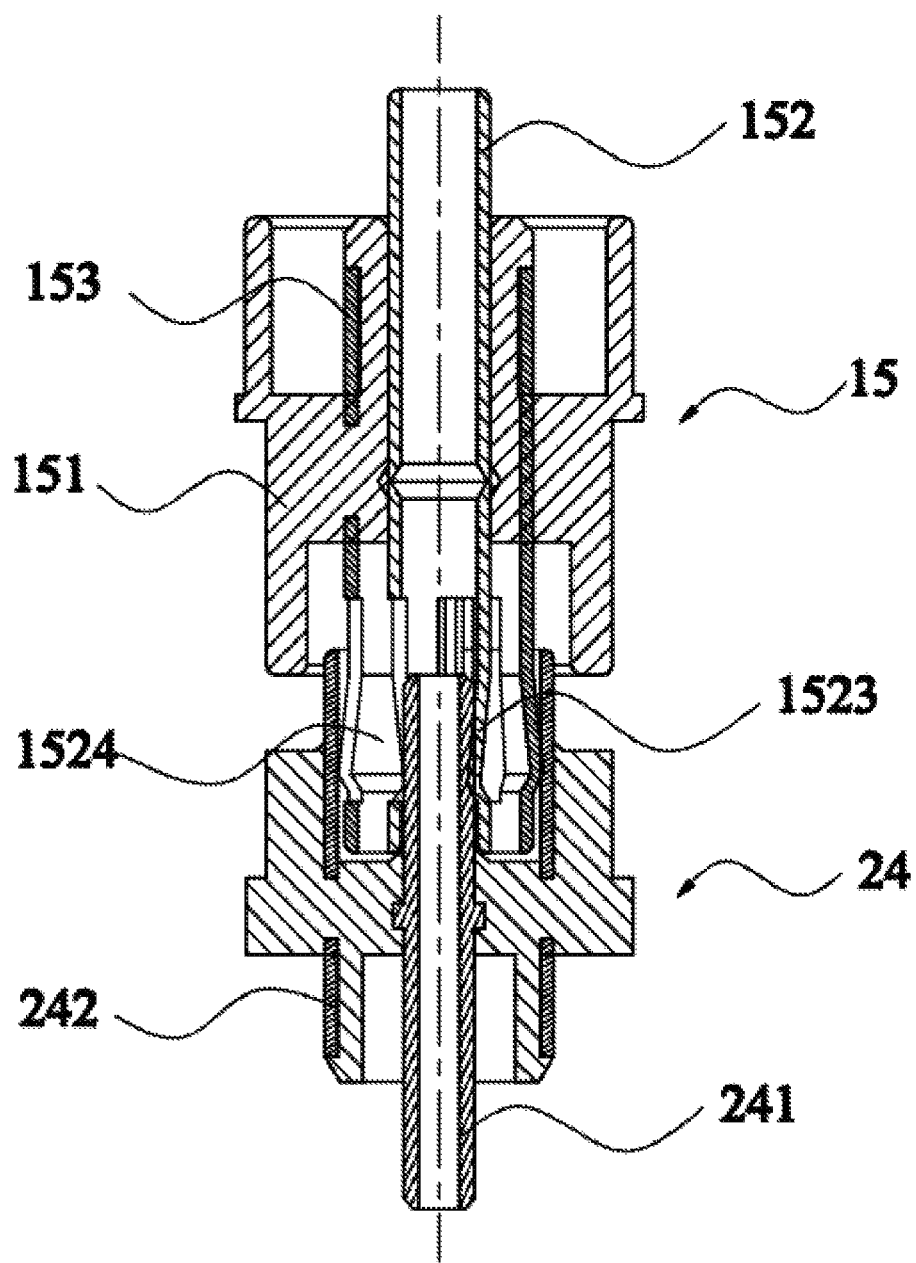
FIG. 8 is a cross-sectional view showing the engagement of the first and the second connectors of FIG. 7.

Referring to FIGS. 7-8, an electronic cigarette 100 includes the atomizing device 1 according to the first embodiment and the battery assembly 2 in accordance with the second embodiment. The first connector 15 couples with the second connector 24 so that the battery assembly 2 powers the atomizing device 1.

In detail, the clamping hands 1523 of the inner electrode 152 clamp the positive electrode 241 at an outer wall of the positive electrode 241 to form electrical connection, and the engaging hands 1533 of the outer electrode 153 engagably contact with an inner wall of the negative electrode 242 to achieve electrical connection when the inner electrode 152 and the outer electrode 153 are simultaneously placed in the annular gap 240 formed between the positive electrode 241 and the negative electrode 242. In this way, the heating wire 14 is electrically connected to the battery 2.

In the present embodiment, the first connector and the second connector are each an integral part. The atomizing device engages with the battery assembly through plug connection of the first and the second connectors. Accordingly, it is easy and convenient to assemble the electronic cigarette. The production efficiency is increased, and the production cost is decreased.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizing device for an electronic cigarette, comprising:
    an atomizing sleeve;
    a liquid chamber in the atomizing sleeve, the liquid chamber being configured for reserving tobacco liquid;
    an atomizing assembly, the atomizing assembly comprising a liquid conducting component and a heating wire wound around the liquid conducting component, the liquid conducting component being configured for absorbing the tobacco liquid from the liquid chamber; and
    a first connector arranged at one end of the atomizing sleeve, the first connector being integrally formed, the first connector comprising an insulated body, an inner electrode and an outer electrode fixed in the insulated body, the insulated body, the inner electrode and the outer electrode being coaxially arranged, two ends of the heating wire being connected to the inner electrode and the outer electrode respectively; wherein
    a clamping portion is formed at an end of the inner electrode, and an inner diameter of the clamping portion decreases from two ends of the clamping portion to a middle of the clamping portion, the clamping portion comprises a plurality of clamping hands, and every two adjacent ones of the plurality of clamping hands cooperatively define a first gap, which allows air pass through;
    an engaging portion is formed at an end of the outer electrode next to the clamping portion, and an outer diameter of the engaging portion increases from two ends of the engaging portion to a middle of the engaging portion, the engaging portion comprises a plurality of engaging hands, and a second gap is simultaneously defined between every two adjacent ones of the plurality of engaging hands corresponding to the first gap defined between every two adjacent ones of the plurality of clamping hands, wherein air passes through the engaging portion and the clamping portion consecutively via the first and second gaps, respectively, to go into the atomizing sleeve and reach the atomizing assembly.

2. The atomizing device of claim 1, wherein the inner electrode comprises a first end and an opposite second end, the first end is connected to one end of the heating wire, the second end is the end of the inner electrode forming the clamping portion.

3. The atomizing device of claim 1, wherein the clamping portion is moved toward the outer electrode when the first connector is engaged with a second connector, and the engaging portion is moved toward the inner electrode when the first connector is engaged with the second connector.

4. The atomizing device of claim 2, wherein the inner electrode is cylindrical.

5. The atomizing device of claim 4, wherein the inner electrode further includes a guiding portion at a distal end of the clamping portion.

6. The atomizing device of claim 1, wherein the insulated body is made of plastic, and the inner and outer electrodes are wrapped around by the insulated body.

7. An electronic cigarette, comprising:
an atomizing device, comprising:
an atomizing sleeve;
a liquid chamber in the atomizing sleeve, the liquid chamber being configured for reserving tobacco liquid;
an atomizing assembly, the atomizing assembly comprising a liquid conducting component and a heating wire wound around the liquid conducting component, the liquid conducting component being configured for absorbing the tobacco liquid from the liquid chamber; and
a first connector arranged at one end of the atomizing sleeve, the first connector being integrally formed, the first connector comprising an insulated body, an inner electrode and an outer electrode fixed in the insulated body, the insulated body, the inner electrode and the outer electrode being coaxially arranged, two ends of the heating wire being connected to the inner electrode and the outer electrode respectively; and
a battery assembly configured for powering the atomizing device, comprising:
a housing;
a battery received in the housing;
a controller electrically connected with the battery; and
a second connector fixed at one end of the housing, the second connector being integrally formed, the second connector comprising a positive electrode, a negative electrode, and an insulated medium, the positive electrode and the negative electrode being coaxially arranged, the insulated medium being configured for fixing the positive electrode and the negative electrode, and keeping the positive electrode and the negative electrode insulated from each other, the positive electrode and the negative electrode being connected to corresponding electrodes of the battery, respectively, the atomizing device being engaged with the battery assembly through plug connection between the first connector and the second connector; wherein a clamping portion is formed at an end of the inner electrode, the clamping portion comprises a plurality of clamping hands, and every two adjacent ones of the plurality of clamping hands cooperatively define a first gap, which allows air pass through;
an engaging portion is formed at an end of the outer electrode next to the clamping portion, the engaging portion comprises a plurality of engaging hands, and a second gap is simultaneously defined between every two adjacent ones of the plurality of engaging hands corresponding to the first gap defined between every two adjacent ones of the plurality of clamping hands, wherein air passes through the engaging portion and the clamping portion consecutively via the first and second gaps, respectively, to go into the atomizing sleeve and reach the atomizing assembly; and
an annular gap is defined between the positive electrode and the negative electrode for receiving the inner electrode and the outer electrode therein.

8. The electronic cigarette of claim 7, wherein the inner electrode comprises a first end and an opposite second end, the first end is connected to one end of the heating wire, the second end is the end of the inner electrode forming the clamping portion.

9. The electronic cigarette of claim 7, wherein, when the first connector is connected with the second connector, the clamping portion is used to clamp the positive electrode at an outer wall thereof and is moved toward the outer electrode by the outer wall of the positive electrode, and the engaging portion is used to engage with an inner wall of the negative electrode and is moved toward the inner electrode by the inner wall of the negative electrode.

10. The electronic cigarette of claim 7, wherein the inner electrode is cylindrical, and an inner diameter of the clamping portion decreases from two ends of the clamping portion to a middle of the clamping portion.

11. The electronic cigarette of claim 7, wherein the inner electrode further includes a guiding portion at a distal end of the clamping portion.

12. The electronic cigarette of claim 7, wherein the insulated body is made of plastic, and the inner and outer electrodes are wrapped around by the insulated body.

13. The electronic cigarette of claim 7, wherein the insulated medium comprises a side surface and at least one protrusion formed on the side surface.

14. The electronic cigarette of claim 13, wherein the side surface is cylindrical.

* * * * *